United States Patent [19]

Cerny

[11] Patent Number: 4,521,038
[45] Date of Patent: Jun. 4, 1985

[54] SAFETY CONNECTOR FOR FLEXIBLE TUBE DEVICE

[75] Inventor: David E. Cerny, Hoffman Estates, Ill.

[73] Assignee: Respiratory Care, Inc., Arlington Heights, Ill.

[21] Appl. No.: 496,558

[22] Filed: May 20, 1983

[51] Int. Cl.³ .............................................. F16L 35/00
[52] U.S. Cl. ........................................ 285/24; 285/93; 285/133 R; 285/179; 285/423; 285/DIG. 4; 128/204.18; 128/911
[58] Field of Search ........................ 285/24, 25, 26, 27, 285/28, 29, 93, 133 R, 179, 423, 332, 260, DIG. 4; 128/200.14, 203.12, 204.18, 204.26, 910, 911, 912; 138/114; 116/DIG. 21

[56] References Cited

U.S. PATENT DOCUMENTS

| | | | |
|---|---|---|---|
| 3,856,051 | 1/1973 | Bain | 138/114 |
| 4,281,652 | 9/1981 | Miller | 128/911 |
| 4,320,754 | 3/1982 | Watson et al. | 128/911 |
| 4,361,107 | 11/1982 | Gereg | 116/DIG. 21 |
| 4,367,769 | 1/1983 | Bain | 138/114 |
| 4,396,015 | 9/1983 | Johnson | 128/200.14 |
| 4,463,755 | 9/1984 | Suzuki | 128/911 |

Primary Examiner—Thomas F. Callaghan
Assistant Examiner—Eric K. Nicholson
Attorney, Agent, or Firm—Eric P. Schellin

[57] ABSTRACT

A flexible tubular assembly having an outer flexible tube through which extends an inner flexible tube which is connected to a tubular element having an elbow-shaped locking piece. The outer flexible tube is joined to the tubular element and the inner flexible tube extends through a cylindrical section of the tubular element to the exterior of the element thereby exposing the end portion of the inner flexible tubing. The spout area of the elbow-shaped locking piece is inserted into the inner flexible tubing and thereby distends the tubing against the sides of an internal tubing and thereby distends the tubing against the sides of an internal tubular stub within the tubular element and locking the tubing in place. Outwardly extending ears on the elbow engage inwardly extending slots on the tubular element thereby holding the elbow in place. The device is specifically useful in anaesthetic devices insuring the safety of a patient.

10 Claims, 7 Drawing Figures

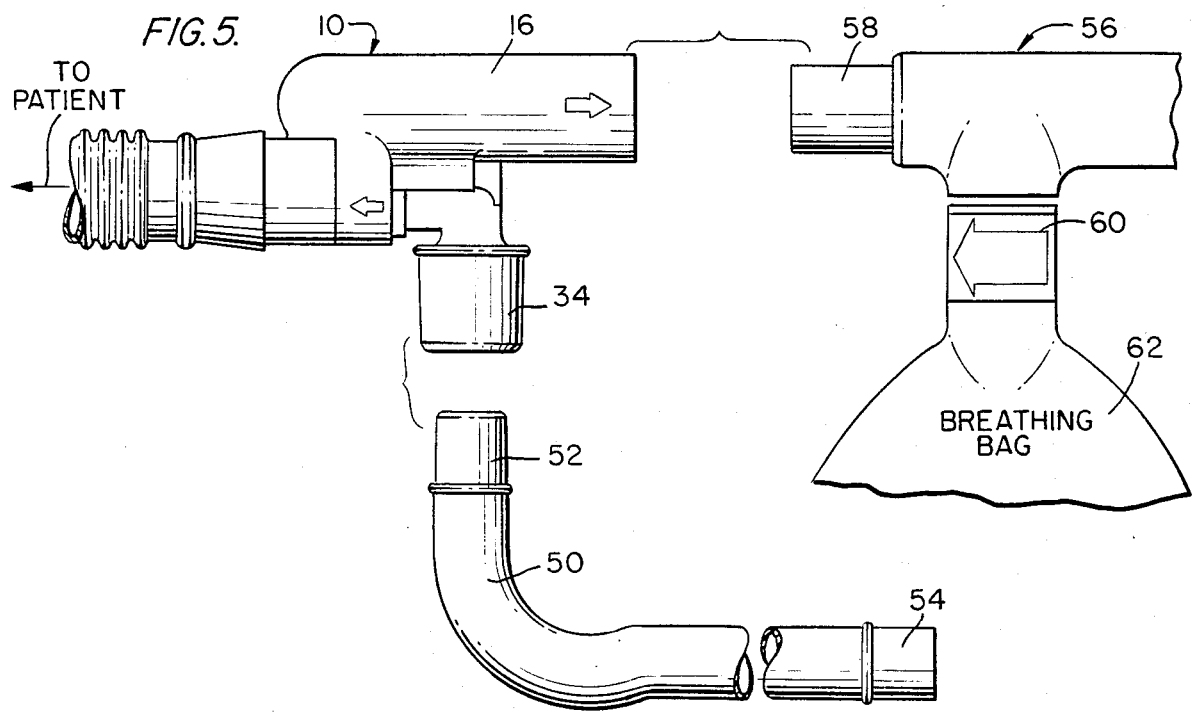
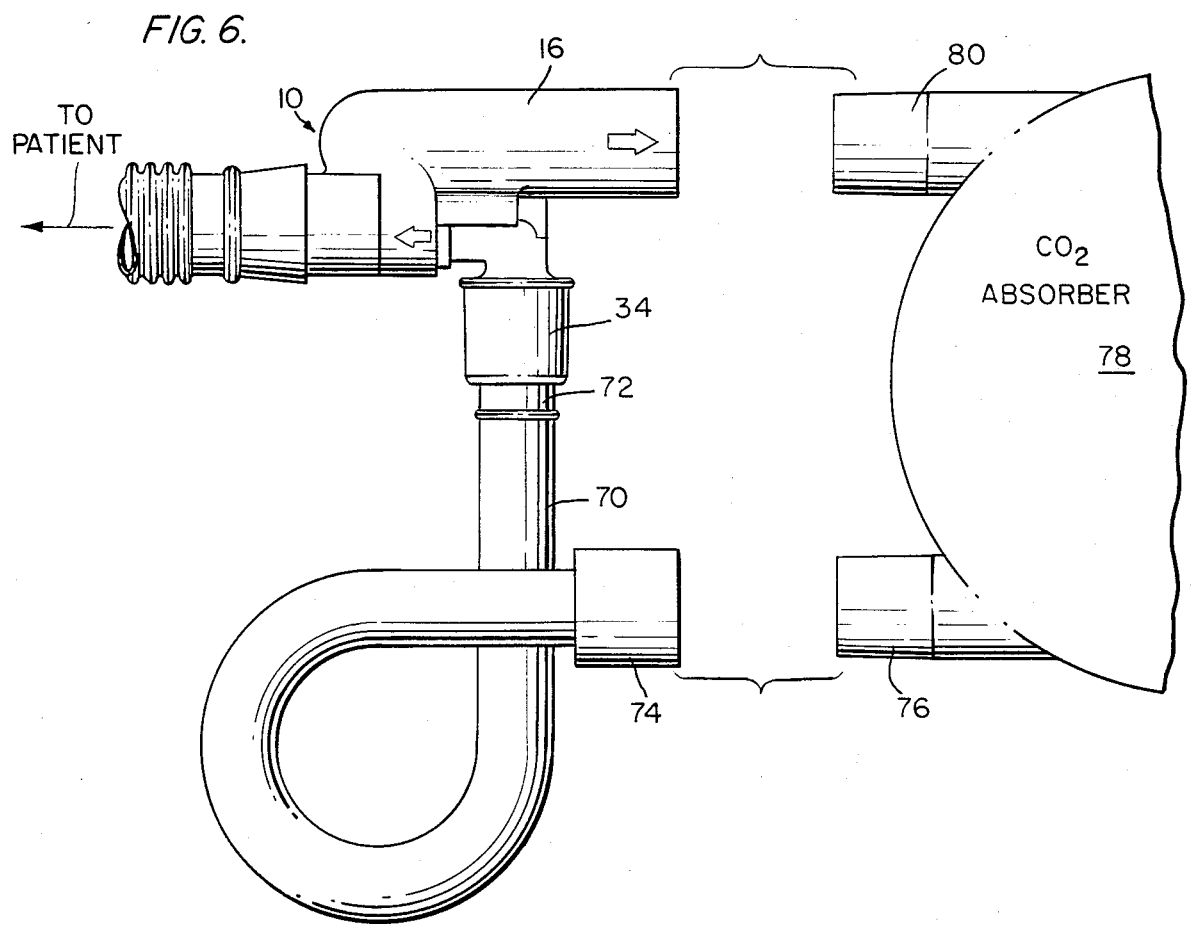

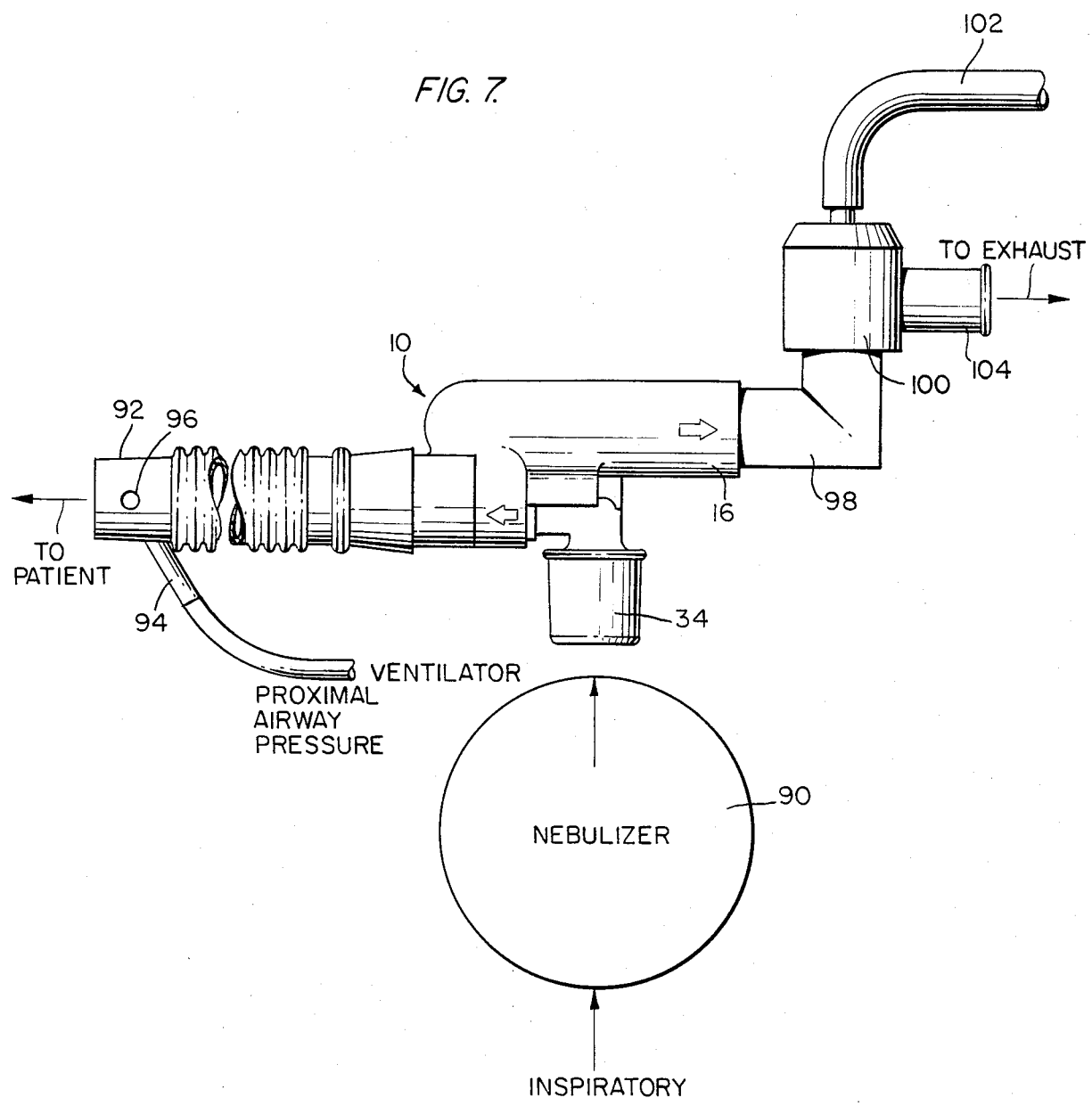

SAFETY CONNECTOR FOR FLEXIBLE TUBE DEVICE

BACKGROUND OF THE INVENTION

1. Field of the Invention

The present invention is related to an anaesthetic device, and more particularly, to a device having a safety connection to insure that the device is in proper working order.

2. Description of the Prior Art

In partial rebreathing anaesthetic systems various types of systems and devices have been disclosed. However, it has been discovered that such systems suffer from convenience of operation and simplicity when they are employed.

In particular, Bain, U.S. Pat. No. 3,856,051, discloses a system and a device which eliminates the use of a plurality of separate tubes for such circuit and provides means for supplying an anaesthetic gas closely to the nasal and oral passages of a patient. It also produces a simpler more convenient means of directing anaesthetic gas to a patient.

In this system a first flexible corrugated thin walled tubular member is employed for exhalation from the patient. Located inside of the first tubular member is a second flexible tubular member of considerably smaller diameter. The second tubular member is designed to carry the anaesthetic gas. One end of each of the tubes terminate at the locale of the patient. The other ends terminate in a tubular rigid connector. The first flexible tubular member terminates externally of one end of said tubular connector. The rigid tubular connector has a tubular elbow which extends through a wall of the rigid tubular connector. The elbow is adapted and constructed to accept the end of the second tubular member internally of said rigid tubular connector.

This connection has proved to be a considerable problem. The device disclosed in the aforementioned patent is designed to be disposable. However, it has been found that the device is in fact employed on repeated occasions. Unfortunately, with a number of uses, including autoclaving, the second flexible tube connected to the elbow has on occasion become disengaged whereby the anaesthetic gas spills into the confines of the first flexible tubular member to the detriment of the patient. Due to the fact that the connection to the elbow with the second flexible tubular member is internally with respect to the rigid tubular connector, one cannot visually inspect the device to determine whether the aforementioned internal connection is still in engagement.

A solution to the above-described problem is disclosed in U.S. patent application Ser. No. 925,393, filed on July 17, 1978, now U.S. Pat. No. 4,367,769. Specifically, the end of the flexible tubular member passes through an external stub on the connector where it is exposed to visual inspection. The flexible tubing is held in place by a nipple which is used in joining the flexible tubing to another flexible tube.

The present invention exposes the end of the flexible tubing as discussed above, by improving the connector by utilizing an internal stud disposed in the tubular connector itself to better protect the connection. In addition, the present invention has an externally mounted elbow locking piece to secure the tubing in place.

SUMMARY OF THE INVENTION

The present invention comprises a tubular connector which is formed from first and second cylindrical elements that are joined to one another at their sides. At the ends of the tubular connector is a first tubular end portion and a second tubular end portion, each being formed by the respective cylindrical elements. An offset annular passage is formed between the two end portions. The first tubular end portion engages a first flexible corrugated tube. An internal tubular stub is disposed inside of the first cylindrical element and therethrough receives the second flexible tubing that extends substantially throughout the first flexible tube. The end portion of the second flexible tube is exposed to the exterior of the tubular element where it can be visually inspected to insure that the tubing is still locked in place.

An elbow shaped locking piece having a spout distends the tubing located in the internal stub thereby locking the tubing in place. Because the spout of the locking piece fits inside of the tubing the end portion of the tubing can still be inspected after the tubing is locked in place.

A guide means is associated with both the second cylindrical element and the elbow for holding the elbow in the proper position. Outwardly extending ears on the elbow engage inwardly extending slots on the second cylindrical element thereby holding the locking piece in the proper position.

BRIEF DESCRIPTION OF THE DRAWINGS

FIG. 5 is a schematic showing the device of the present invention in a conventional re-breathing circuit;

FIG. 6 is a schematic showing the device of the present invention in a conventional "circle" circuit; and FIG. 7 is a schematic showing the device of the present invention in a ventilator circuit.

DETAILED DESCRIPTION OF THE INVENTION

Figure 1:
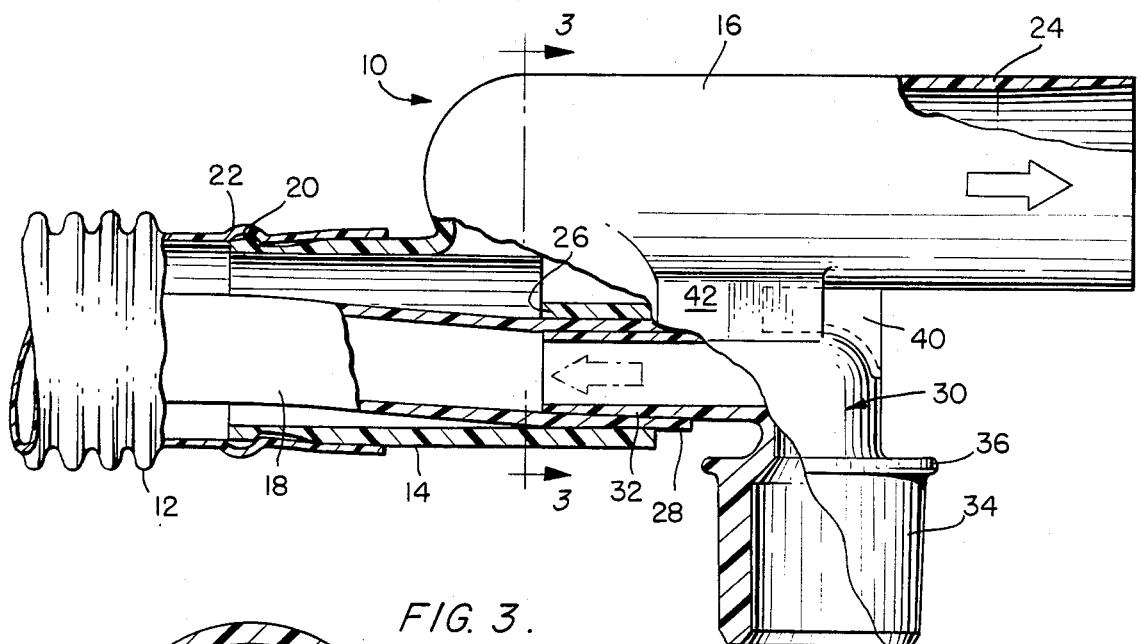
FIG. 1 is a partial sectional view of the present invention illustrating the tubular connector, the flexible tubing and the elbow-shaped locking piece.

Referring to FIG. 1, tubular element 10 frictionally engages corrugated flexible conduit 12. Tubular element 10 comprises first cylindrical element 14 and second cylindrical element 16 through which an annular offset passage is formed. As in the prior art of U.S. Pat. Nos. 3,856,051 and 4,367,769, a second flexible tubular member 18 extends through conduit 12 and may be attached to the sidewalls of conduit 12 by appropriate means, such as by solvent binding or adhesives.

First cylindrical element 14 forms a first tubular end portion which comprises a tapered portion terminating in lip 20. Lip 20 is designed to mate with indentation 22 of the end portion of conduit 12. Similarly, second cylindrical element 16 forms a second tubular end portion that has internal taper 24 which facilitates connecting the tubular element to another device, not shown.

Figure 3:
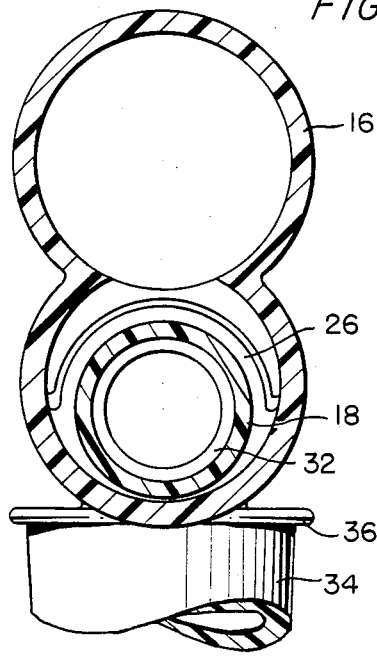
FIG. 3 is a sectional view along line 3—3.

Of particular importance, is internal tubular stub 26 through which conduit 18 passes. As can be readily determined from FIGS. 1 and 3, stub 26 has an external diameter that is less than the internal diameter of first cylindrical element 14. Tubing 18 has an external diameter that is less than the internal diameter of stub 26 so that it may easily be slipped into the stub.

End portion 28 of tubing 18 extends beyond stub 26 and out through an opening into the exterior of the connector. As such, it can be visually determined by the operator of the system if tubing 18 has become dislodged in the connector. The visual preception of the operator can be heightened by providing that tubing 18 be a different color than that of tubular element 10. Alternatively, tubing 18 and end portion 28 can be made of an opaque material that obscures a warning when properly positioned. Therefore, if the tubing becomes dislodged, the warning is uncovered and the operator is alerted.

Tubing 18 is locked in place by elbow-shaped locking piece 30. More specifically, spout 32 of the locking piece fits inside of the tubing located inside of stub 26 distending the tubing and locking it in the appropriate position. Spout 32 is provided with a slight external inward taper to ease in placement of the spout and to aid in locking the tubing in place. Locking piece 30 also comprises an annular bell 34 having annular rim 36. Bell 34 is normally connected to the anaesthetic gas supply which is not shown in the present drawings.

Figure 2:
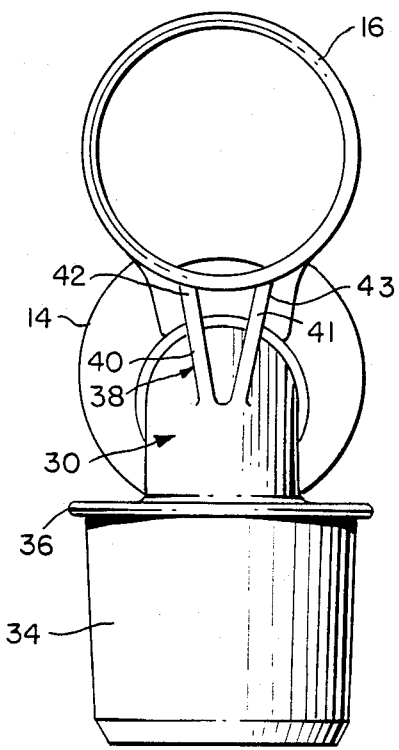
FIG. 2 is a rear view of the present invention illustrating the guide means.
Figure 4:
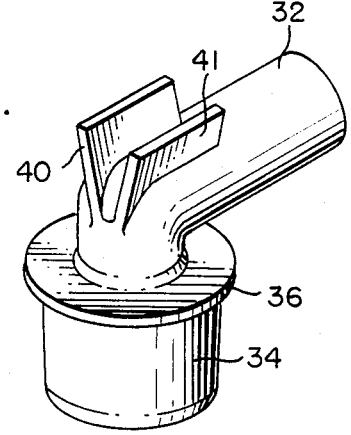
FIG. 4 is a perspective view of elbow-shaped locking piece.

Guide means 38, best illustrated in FIG. 2, aids in guiding and holding locking piece 30 in the correct locking position. Guide means 38 comprises outwardly extending ears 40 and 41 which are mounted on spout 32 of the locking piece; and inwardly extending slots 42 and 43 thereby guiding the locking piece and preventing the locking piece from twisting and working loose.

It is now appropriate to turn to FIGS. 5, 6 and 7 for a review as to the many uses for the connector in medical technology and delivery systems.

In FIG. 5, for instance, it will be seen that a reusable fresh gas line 50 having a suitable attachment means 52 at one end is friction fitted internally of bell 34. Line 50 is supplied at its other end with a suitable fitment 54 which in turn is secured to a conventional and appropriate fitment leading to a source of fresh gas, not shown. The exhaust side 16 is connected to a conventional Tee-connector 56 having a suitable fitment 58 that is capable of being friction fitted internally of said exhaust side. The downwardly directed leg 60 of the Tee-connector 56 has a conventional breathing bag 62. The set-up described is used in a conventional manner.

FIG. 6 describes what is known as a "circle" administration of gases. Again, the connector 10 of the present invention is fitted to a conduit 70 having at one end a fitment 72 which is frictionally engageable internally of bell 34. The other end is supplied with a fitment having means internally thereof to be friction fitted with an egress port means 76 of a carbon dioxide absorber 78. The ingress port means 80 is frictionally internally engageable with the exhaust side 16 of the connector of the present invention. As one would suppose the set-up of this figure is designed to permit carbon dioxide removal whereby expensive anaesthetic gases may be re-cycled.

In the embodiment of FIG. 7 fluid circuitry is shown that employs the connector of the present invention in association with a nebulizer and exhaust valving control means in a ventilator system. The nebulizer and the valving system may be of the type disclosed in a patent application Ser. No. 500,812 filed on 6/3/83 of the present applicant entitled: SELF-CONTAINED NEBULIZER AND SYSTEM, filed concurrently herewith; said application is incorporated herewith by reference.

The ventilator system may be used for neonatal, infant and adult treatment. The bell 34 is connected to the dispensing side of a conventional nebulizer 90 which may be of the type disclosed in the said patent application. The nebulizer may be of the type that includes a heater for the moisturized gas (usually air or a higher oxygen concentration gas). The nebulized gas carrying tube 18 terminates at the proximate end of conduit 12 at a fitting 92 to which an appropriate conduit line is attached for distribution to a patient. This fitting 92 is also supplied through conduit 94 with proximal airway pressure as necessary. It will be noted that the fitting 92 is also supplied with a port 96 for a temperature probe, necessary when heat is supplied to the nebulizer 90. The element 16 has fitted thereto a conduit 98 which in turn carries an exhaust valve means 100 which opens when the line pressure supplied to the valve by means of the opposite side of a diaphragm valve (not shown in detail) by means of conduit 102. The excess gas pressure is relieved or dumped at egress port 104. The design of the system is to thereby control not only the pressure of gases supplied the patient but also the amount of moisture and the temperature of the gas thusly delivered.

The present invention can also be adapted for other non-anaesthetic uses where a connector is needed for conduits having coaxially disposed flexible tubing. So while the present invention has been disclosed in connection with the illustrated embodiment, it is not to be so limited but is to be limited solely by the claims that follow.

I claim:

1. A connector comprising:

a rigid tubular element comprising a first cylindrical element which is joined at its side to a second cylindrical element;

a first tubular end portion is formed by said first cylindrical element;

a second tubular end portion is formed by said second cylindrical element;

an offset flow passage is formed between said first tubular end portion and said second tubular end portion;

a first flexible tubing having an end portion concentrically frictionally positioned on said first end portion;

an internal tubular stub having an external diameter less than the internal diameter of said first cylindrical element is disposed within said first cylindrical element and has an opening that communicates with the exterior of said tubular element;

a second flexible tubing having an external diameter that is less than the internal diameter of said internal tubular stub, extends through said first flexible tubing and is inserted through said internal tubular stub and extends beyond said stub to the exterior of said tubular element providing a visible exposed end position of said second flexible tubing;

an elbow-shaped locking piece having a spout that is frictionally positioned within said second flexible tubing thereby locking said second flexible tubing within said stub; and guide means associated with said second cylindrical element and elbow-shaped locking piece which hold said locking piece in proper position.

2. A connector in accordance with claim 1 wherein said spout of said elbow-shaped locking piece has an external inward taper for facilitating the locking of said second flexible tubing within said internal tubular stub.

3. A connector in accordance with claim 2 wherein said first tubular end portion has a lip which is used to mate with a matching indentation on said end portion of said first flexible tubing.

4. A connector in accordance with claim 3 wherein said second tubular end portion has an internal taper.

5. A connector in accordance with claim 4 wherein said guide means comprises outwardly extending ears on said elbow shaped locking piece and inwardly extending slots on said second cylindrical element.

6. A connector in accordance with claim 5 wherein said second flexible tubing is a different color than said tubular element so that said exposed end portion of said second flexible tubing can be easily detected.

7. A connector in accordance with claim 6 wherein said tubular element is made of plastic.

8. A connector in accordance with claim 7 wherein said elbow-shaped locking piece is made of plastic.

9. A connector in accordance with claim 8 wherein said first flexible tubing is corrugated.

10. A connector in accordance with claim 5 wherein said second flexible tubing is opaque and said exposed end portion obscures a warning when properly positioned.

* * * * *